US00PP36336P2

(12) United States Plant Patent
Shipley et al.

(10) Patent No.: US PP36,336 P2
(45) Date of Patent: Dec. 24, 2024

(54) ***LEUCOPHYLLUM* PLANT NAMED 'Laredo'**

(50) Latin Name: ***Leucophyllum frutescens* X *zygophyllum***
Varietal Denomination: Laredo

(71) Applicants: Nicholas Benoit Shipley, Tucson, AZ (US); Russ A. Buhrow, Tucson, AZ (US)

(72) Inventors: Nicholas Benoit Shipley, Tucson, AZ (US); Russ A. Buhrow, Tucson, AZ (US)

( * ) Notice: Subject to any disclaimer, the term of this patent is extended or adjusted under 35 U.S.C. 154(b) by 0 days.

(21) Appl. No.: 18/445,784

(22) Filed: Feb. 2, 2024

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./226
See application file for complete search history.

*Primary Examiner* — Susan McCormick Ewoldt

(57) ABSTRACT

A new and distinct *Leucophyllum frutescens* X *zygophyllum* plant named 'Laredo' is characterized as a many branched, rounded shrub reaching a size of 5 feet tall×6 feet wide by age 5, with silvery leaves and a generally cloudlike appearance, winterfast leaves, pleasantly fragrant flowers colored N82B (strong purple) that last about 3 days and do not fade with age, as well as possessing excellent resistance to damping off diseases. 'Laredo' is hardy to USDA zone 7B/8A.

2 Drawing Sheets

Latin name: *Leucophyllum frutescens* X *zygophyllum*.
Varietal denomination: 'Laredo'.

INTRODUCTION

Shrubs of the genus *Leucophyllum* are commonly called Texas Rangers, simply "Rangers" or barometer plant in English and Cenizo in Mexico. The genus consists of about 12 species native to arid portions of Mexico from Puebla in the south northward to the southern portions of Texas. The various "Rangers" have become popular landscape plants throughout the southwestern United States as well as other areas of the world with similar climates and extending into moister areas successfully if the soil has adequate drainage. Seven species of *Leucophyllum* are commonly cultivated, as well as several interspecific hybrid cultivars. The most popularly grown species is *Leucophyllum frutescens*. Several cultivars of this species are grown.

BACKGROUND OF THE INVENTION

The present invention relates to a new and distinct cultivar of *Leucophyllum zygophyllum*. The cultivar originated from an intentional breeding program designed to create new cultivars with improved nursery and landscape performance, as many current *Leucophyllum* cultivars are susceptible to damping off diseases both in the nursery and in the landscape. Cultivars are also being selected for other horticultural characteristics such as mature plant size, density and reduced maintenance costs as well as improvement of flowering characteristics. In the $F_2$ generation of the cross *Leucophyllum frutescens* 'Green Cloud' (unpatented) X *Leucophyllum zygophyllum* (proprietary breeding line) a plant was produced with greatly improved resistance to root rots and possessing an appearance similar to commercially available *Leucophyllum zygophyllum* but with a reduced mature size as well as a dense form allowing reduced maintenance and is the object of this application.

SUMMARY OF THE INVENTION

Among the features that distinguish the new *Leucophyllum* cultivar from all other available and commercial varieties of *Leucophyllum* known to the inventor are the following combination of characteristics: a many branched, rounded shrub reaching a size of 5 feet tall×6 feet wide by age 5, with silvery, winterfast leaves and a generally cloudlike appearance, pleasantly fragrant flowers that do not fade with age colored N82B and lasting about 3 days, as well as excellent resistance to damping off diseases. Typically, *Leucophyllum* cultivars exhibit considerable leaf drop during winter. 'Laredo' has winter fast leaves, meaning reduced leaf drop and less winter leaf discoloration of remaining leaves, presenting a more attractive winter form than many other *Leucophyllum* cultivars. No insect or disease problems have been noted with this plant. 'Laredo' is hardy to at least 10° F., USDA zone 7B/8A. 'Laredo' is propagated asexually at a commercial nursery located near Sahuarita, Arizona.

The asexual propagation procedure is as follows: Semi-hardwood cuttings 4-5" long are prepared by removing the lower leaves, then dipping the cleared portion of the cut into a 1:10 solution of DIP'N GROW™. The cuttings are then inserted about one inch into prepared peat trays. The trays are moved to a mist house with mist applied every 20 minutes and temperature maintained between 70-85° F. Rooting is generally complete within 4 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Leucophyllum zygophyllum* 'Laredo' growing near Sahuarita, Arizona, depicted in color as nearly correct as it is possible to make in a color illustration of the character.

DETAILED PLANT DESCRIPTION

Figure 1:
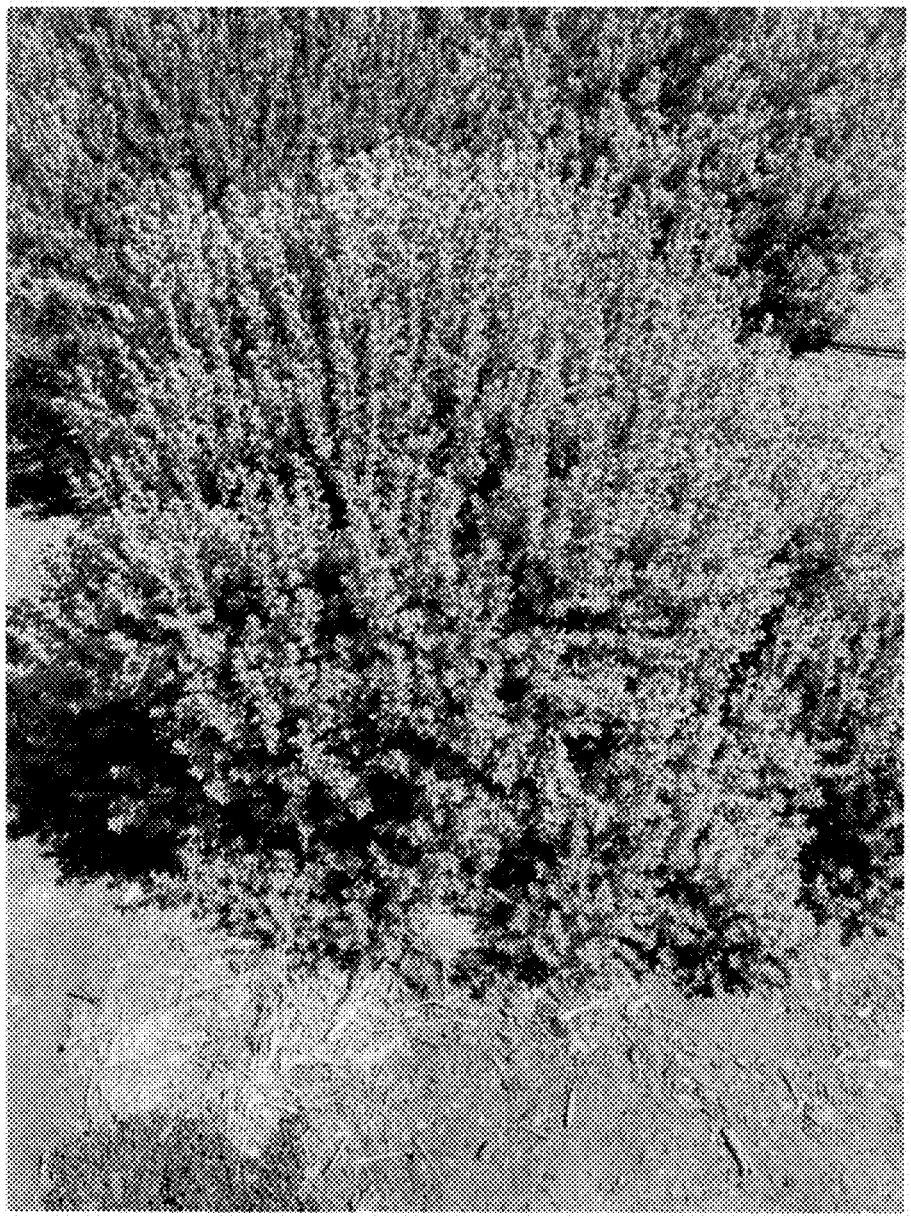
FIG. 1 shows 'Laredo' growing in a commercial nursery near Sahuarita, Arizona at age 5 years.
Figure 2:
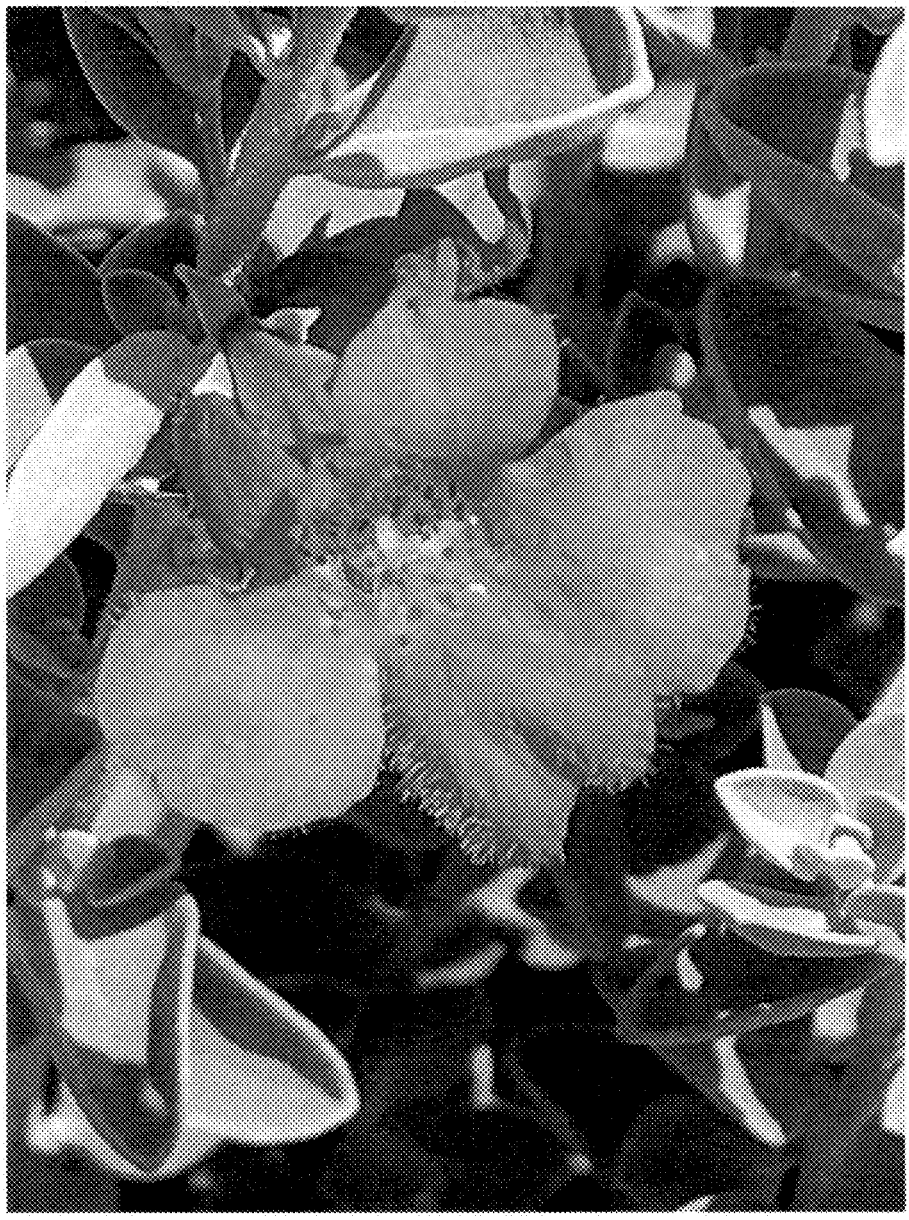
FIG. 2 illustrates 'Laredo' flowers, leaves and stems.

The following is a detailed description of the new *Leucophyllum* plant based upon the original plant at age 5 years growing in the ground near Sahuarita, Arizona as well as a cloned plant growing in a #5 nursery pot in Tucson, Arizona.

The color descriptions are based upon the 5$^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant a many branched, dense, rounded shrub reaching 5 feet tall×6 feet wide at age 5 years under irrigation if unpruned. Plant presents a soft, cloudlike appearance with silvery leaves and with trumpet shaped, pleasantly fragrant flowers colored N82B which appear intermittently from April through November at the Sahuarita, Arizona location. Flowering is heaviest in late summer through mid-autumn.

Young stems are terete, measuring 0.9-1.3 mm in diameter. The stems are densely covered with multibranched stellate hairs colored 155C. The stem base color is 138B. Internodes vary from 2-8 mm in length. Older stems become reticulate with age and the hairs become caducous. These stems are uniformly colored closest to 200D. Stem branch angles vary from 45-60°. Plants growing in #5 nursery containers averaged 88 stems with an average length of 9.3 cm.

Axillary buds are ovoid in shape, measuring 0.6 mm in length and 0.3 mm in diameter. The surface is densely covered with hairs, appearing wooly, the hairs colored. 192D. The bud surface is completely obscured by the hairy covering.

Leaves are sessile, alternate, obovate, apex rounded, base broadly acute with obscure pinnate venation. The leaf margin is entire. The leaves are slightly folded adaxially along the midvein. Leaves are densely canescent with stellate hairs, more so on the abaxial surface and even heavier along the raised abaxial midvein. The adaxial midvein is depressed below the general surface. The leaf base color is 138B (both surfaces) and the surface hairs are colored 155C. The leaf midvein is colored 138B. Leaves measure 7-20 mm long× 6-12 mm wide.

Pedicels are terete, 3.5 mm long×0.6 mm diameter, colored 143C, canescent with stellate hairs colored NN155D. Calyx somewhat spreading, 5 lobed, basally united, 6 mm long, 3 mm diameter at calyx base, 6 mm diameter at the apex. Calyx lobes lanceolate, basally truncate, apically acute, margins entire, colored 143C, measuring 4-6 mm long×2 mm wide at the base, abaxially canescent with stellate hairs which are densest at the base, hairs colored NN155D. Adaxial lobe surface is colored 143C covered with scattered, short hairs colored NN155D.

Flower buds are oblanceoloid, glabrous, measuring 14.5 mm long×5 mm wide at the widest part. Longitudinally the upper ⅓ of the tube is colored N81B and the lower ⅔ is colored N155A.

Flowers are solitary in the leaf axils.

Flowers are trumpet shaped, 5 lobed, the lobes orbicular, margins entire, somewhat crisped, lobes measuring 9-10 mm wide×9-10 mm long, flared and somewhat extended, the lowest lobe more so. Flowers measure 22-26 mm long, 20-22 mm wide, 15-20 mm high. The tube opening at the petal lobes measures 6-7 mm wide×4 mm high. The two upper lobes are glabrous, colored N82B. The two lateral petal lobes are ciliate with straight hairs colored N82B about 0.5 mm long, these becoming somewhat caducous as the flower ages. Adaxially these lobes are colored N82B. The lowest petal lobe is densely covered with straight hairs about 1 mm long colored like the lowest petal lobe, N82B. The petal lobe exteriors (abaxially) are glabrous, colored N82D. The floral tube externally has a longitudinal vein aligned with the midpoint of the two upper petal lobes measuring 1.5 mm wide colored N82B, grading to N82D in the adjacent area of the longitudinal upper ½ of the tube. The longitudinal lower half is colored 76C. Internally the upper medial vein measures 1.5 mm wide, color N82B. The remaining internal tube is colored NN155C with spots measuring from 0.3-0.5 mm in diameter colored 165B. The terminal half of the tube is covered with wavy hairs up to 3 mm long on the longitudinal lower ¼ of the tube, these densest near the mouth of the throat and colored NN155D.

Staminode absent. Stamens 4, of equal length, didynamous, epipetalous, measuring 7 mm long. Filament 4.25 mm long, terete, diameter 0.6 mm, colored NN155B. Anthers measuring 2.75 mm long×2 mm wide×0.75 mm thick, color 155B. Nearly spherical pollen measures 30 μ in diameter colored 155D.

Pistil measures 13.5 mm long. Ovary conical, glabrous, 3.25 mm long×2.0 mm in diameter, color 146D. Style terete, curved, 9-10 mm long, diameter 0.5 mm, flared apically just below the stigma, color 84A. Stigma follows the flare of the style measuring 1.25 mm long and 0.6 mm thick, colored 84A.

A nearly mature fruit was examined. The surface was hardened but the seeds were still immature. The fruit is ovoid, compressed on the septum sides, measuring 5 mm long×3 mm wide×2 mm thick. The fruit apex is apiculate and colored N78A. The fruit has 2 carpels and contains about 20 seeds. The fruit is glabrous, color 137A. At maturity *Leucophyllum* fruits dehisce on both the septum and carpel lines, but these fruits had not dehisced. The observed, immature seeds were oblongoid, translucent, measuring 1 mm long×0.3 mm in diameter. Seed color was 153C. 'Laredo' has demonstrated excellent resistance to damping off diseases both in the nursery and in the ground. 'Laredo' is hardy to USDA zone 7B/8A. No insect problems or diseases were noted.

COMPARISONS TO RELATED *LEUCOPHYLLUMS*

Compared to its female parent, *Leucophyllum frutescens* 'Green Cloud' (unpatented), 'Laredo' is about ½ the size of 'Green Cloud'. The flowers of 'Green Cloud' are colored 64D compared to N82B (strong purple) for those of 'Laredo'.

Compared to its male parent, *Leucophyllum zygophyllum* (unpatented), 'Laredo' is a smaller plant (5×6 feet compared to 7×7 feet). The flowers of *Leucophyllum zygophyllum* are colored N88C while those of 'Laredo' are colored N82B. 'Laredo' has much improved resistance to damping off diseases compared to its male parent. Of all known cultivars of *Leucophyllum* available, 'Laredo' is the closest in appearance to its male parent.

Compared to *Leucophyllum frutescens* 'San Antonio Rose', (U.S. Plant Pat. No. 33,454-P2), flowers of 'San Antonio Rose' measure across the lateral flower face 19-24 mm, color 75A (light purple) while those of 'Laredo' measure 20-22 mm wide, color N82B (strong purple). Floral fragrance of 'Laredo' similar in strength to that 'San Antonio Rose' but differs in scent "flavor" for lack of a better term.

Compared to *Leucophyllum frutescens* 'Convent' (unpatented), 'Laredo' has a rounded shape while 'Convent' is more upright in growth habit. 'Convent' flowers are colored N74B (vivid reddish purple) while those of 'Laredo' are colored N82B (strong purple). 'Convent' is highly susceptible to damping off but damping off has not been observed in the nursery or in the ground with 'Laredo'.

Compared to *Leucophyllum frutescens* 'Compacta' (not patented), 'Laredo' is a smaller plant with flowers colored N82B (strong purple) while those of 'Compacta' are colored 75A (light purple).

Compared to 'Heavenly Cloud' (not patented), an interspecies hybrid between *Leucophyllum frutescens* and *L. laevigatum*, 'Laredo' is about ⅔ as large. Flowers of 'Laredo' are colored N82B (strong purple) compared to 94C (brilliant purplish blue) for 'Heavenly Cloud'.

Compared to *Leucophyllum frutescens* 'White Cloud' (not patented), 'Laredo' is ½ as large. 'White Cloud' has white flowers compared to those of 'Laredo', colored N82B (strong purple). Damping off resistance is stronger in 'Laredo'.

Compared to *Leucophyllum* hybrid 'MSWNRascon' (U.S. Plant Pat. No. 33,806-P2), 'Laredo' has a rounded form compared to an upright, spreading form for 'MSWNRascon'. The flowers of 'MSWNRascon' are colored 77A, 77B (deep reddish purple, strong purple) while those of 'Laredo' are colored N82B (strong purple). The mature size of 'MSWNRascon' is listed as 6-8' while 'Laredo' grows to 5'×6'.

Compared to *Leucophyllum frutescens* 'GREHJS' (U.S. Plant Pat. No. 33,638-P2), 'Laredo' has 5 flower petal lobes colored N82B (strong purple), while 'GREHJS' has 6 petal lobes of differing colors, the upper ones colored 75A (light purple). The growth habit of 'GREHJS' is upright and spreading, while 'Laredo' is rounded.

Compared to 'MSWNHelei' (U.S. Plant Pat. No. 34,884-P2), a low growing shrub with a mounding habit, 'Laredo' is rounded in shape. The flowers of 'MSWNHelei' are colored N82B (strong purple) compared to those of 'Laredo' which are also colored N82B. The leaves of the two cultivars differ in color, with 'Laredo' uniformly colored 138B (moderate yellow green), while those of 'MSWNHelei' are colored 138A (moderate yellowish green) on the upper surface and 146A on the lower surface.

Compared to 'Purple Rain' (U.S. Plant Pat. No. 35,354), 'Laredo' is about ⅔ as large, with flowers colored N82B (strong purple) compared to 80D (light purple) for 'Purple Rain'.

Compared to *Leucophyllum langmaniae* 'Lynn's Legacy' (unpatented), 'Laredo' is about ⅔ as large and rounded, compared to broader than tall for 'Lynn's Legacy'. 'Lynn's Legacy' reaches 6+ feet tall by 10 feet wide under Sahuarita conditions, while 'Laredo' reaches about 5×6 feet. The flower color is 76A (light purple) for 'Lynn's Legacy' and N82B (strong purple) for 'Laredo'. 'Laredo' has improved damping off resistance compared to 'Lynn's Legacy'.

Compared to 'Microburst' (U.S. Plant Pat. No. 35,437), 'Laredo' is larger. The flowers of 'Microburst' are colored N88B (strong violet) and those of 'Laredo' colored N82B (strong purple). The fragrance of 'Microburst' flowers has similar strength to those of 'Laredo'. Both cultivars have excellent resistance to damping off diseases. 'Laredo' has not been tested under the extreme conditions of standing water that 'Microburst' survived unscathed, but both cultivars experience zero loss under the nursery and landscape conditions so far encountered.

Compared to 'Little Lynn' (application Ser. No. 18/445,793), 'Laredo' is about 50% larger. The flowers measure laterally 21-32 mm wide for 'Little Lynn' and 20-22 mm for 'Laredo'. Flowers of 'Little Lynn' are colored 76B (very light purple) while those of 'Laredo' are colored N82B (strong purple).

We claim:

1. A new and distinct *Leucophyllum* plant named 'Laredo' substantially as described and illustrated herein.

* * * * *